(12) United States Patent
Weinberg

(10) Patent No.: US 9,772,387 B2
(45) Date of Patent: Sep. 26, 2017

(54) METHOD AND APPARATUS FOR HIGH RESOLUTION PHYSIOLOGICAL IMAGING OF NEURONS

(71) Applicant: WEINBERG MEDICAL PHYSICS LLC, Bethesda, MD (US)

(72) Inventor: Irving N. Weinberg, Bethesda, MD (US)

(73) Assignee: Weinberg Medical Physics, Inc., North Bethesda, MD (US)

( * ) Notice: Subject to any disclaimer, the term of this patent is extended or adjusted under 35 U.S.C. 154(b) by 1157 days.

(21) Appl. No.: 13/903,137

(22) Filed: May 28, 2013

(65) Prior Publication Data
US 2013/0257428 A1 Oct. 3, 2013

Related U.S. Application Data

(63) Continuation-in-part of application No. 12/888,580, filed on Sep. 23, 2010, now Pat. No. 8,836,329, which is a continuation-in-part of application No. 12/488,105, filed on Jun. 19, 2009, now Pat. No. 8,154,286, application No. 13/903,137, which is a continuation-in-part of application No. 12/905,256, filed on Oct. 15, 2010, now Pat. No. 8,466,680, which is a continuation-in-part of application No. 12/488,105, filed on Jun. 19, 2009, now Pat. No. 8,154,286, application No. 13/903,137, which is a continuation-in-part of application No. 13/439,382, filed on Apr. 4, 2012, now Pat. No. 9,411,030, which is a continuation-in-part of application No. 12/488,105.

(60) Provisional application No. 61/652,223, filed on May 27, 2012, provisional application No. 61/074,397, filed on Jun. 20, 2008, provisional application No.
(Continued)

(51) Int. Cl.
G01R 33/48 (2006.01)
A61B 5/055 (2006.01)
A61B 5/05 (2006.01)
A61B 5/00 (2006.01)

(52) U.S. Cl.
CPC ........ *G01R 33/4806* (2013.01); *A61B 5/0042* (2013.01); *A61B 5/055* (2013.01); *A61B 5/0515* (2013.01)

(58) Field of Classification Search
CPC ... G01R 33/4806; A61B 5/055; A61B 5/0042; A61B 5/0515
See application file for complete search history.

(56) References Cited

U.S. PATENT DOCUMENTS 6,132,360 A * 10/2000 Halpern ............... A61N 2/00
128/898
6,799,141 B1 * 9/2004 Stoustrup ............ H04L 25/0214
342/192
(Continued)

OTHER PUBLICATIONS

Anker et al.; Magnetically modulated optical nanoprobes; Applied Physics Letters; Feb. 17, 2003; pp. 1102-1104; vol. 82, No. 7.
(Continued)

*Primary Examiner* — Dixomara Vargas
(74) *Attorney, Agent, or Firm* — Barnes & Thornburg LLP

(57) ABSTRACT

In accordance with disclosed embodiments, very high magnetic gradients and magnetic slew are applied to magnetizable particle imaging in order to realize high spatial resolution.

15 Claims, 3 Drawing Sheets

Related U.S. Application Data

61/074,394, filed on Jun. 20, 2008, provisional application No. 61/804,094, filed on Mar. 21, 2013.

(56) References Cited

U.S. PATENT DOCUMENTS

| | | | | |
|---|---|---|---|---|
| 7,498,811 B2* | 3/2009 | MacFarlane | ........... | G01R 33/28 324/318 |
| 7,575,934 B2* | 8/2009 | Atwood | ................. | B82Y 15/00 436/165 |
| 7,911,207 B2* | 3/2011 | MacFarlane | ........... | G01R 33/28 324/307 |
| 7,977,942 B2* | 7/2011 | White | ................. | G01R 33/28 324/307 |
| 8,119,976 B2* | 2/2012 | Squier | ................... | G21K 1/006 250/251 |
| 8,154,286 B2 | 4/2012 | Weinberg | | |
| 8,390,291 B2* | 3/2013 | MacFarlane | ........... | G01R 33/28 324/318 |
| 8,697,029 B2* | 4/2014 | Anker | .................... | G01N 33/58 424/1.11 |
| 8,766,633 B2* | 7/2014 | Bhattacharya | ......... | A61B 5/055 324/307 |
| 9,207,296 B2* | 12/2015 | Bhattacharya | ......... | A61B 5/055 |
| 2004/0058458 A1* | 3/2004 | Anker | ................. | G01N 33/587 436/526 |
| 2004/0061967 A1* | 4/2004 | Lee | ....................... | G11B 21/02 360/75 |
| 2006/0008924 A1* | 1/2006 | Anker | ................. | G01N 33/587 436/526 |
| 2007/0108978 A1* | 5/2007 | MacFarlane | ........... | G01R 33/28 324/318 |
| 2008/0011977 A1* | 1/2008 | Atwood | ................. | B82Y 15/00 252/62.51 R |
| 2009/0039235 A1* | 2/2009 | MacFarlane | ........... | G01R 33/28 250/206.1 |
| 2009/0039886 A1* | 2/2009 | White | .................... | G01R 33/28 324/318 |
| 2010/0069726 A1* | 3/2010 | Levinson | ............ | G01N 33/543 600/309 |
| 2011/0068791 A1 | 3/2011 | Weinberg | | |
| 2011/0089947 A1 | 4/2011 | Weinberg et al. | | |
| 2011/0095759 A1* | 4/2011 | Bhattacharya | ......... | A61B 5/055 324/307 |
| 2011/0181893 A1* | 7/2011 | MacFarlane | ........... | G01R 33/28 356/615 |
| 2011/0230755 A1* | 9/2011 | MacFarlane | ........... | A61B 5/055 600/414 |
| 2012/0223711 A1 | 9/2012 | Weinberg | | |
| 2013/0257428 A1* | 10/2013 | Weinberg | ........... | G01R 33/4806 324/309 |
| 2015/0022204 A1* | 1/2015 | Bhattacharya | ......... | A61B 5/055 324/309 |
| 2015/0313995 A1* | 11/2015 | Hung | ................ | A61M 37/0069 600/12 |
| 2016/0282255 A1* | 9/2016 | Irimia | .............. | G01N 33/54326 |

OTHER PUBLICATIONS

Devita et al.; High resolution MRI of the brain at 4.7 Tesla using fast spin echo imaging; The British Journal of Radiology; 2003; pp. 631-637; vol. 76.

Weinberg et al.; Increasing the oscillation frequency of strong magnetic fields above 101 kHz significantly raises peripheral nerve excitation thresholds; Medical Physics Letter; May 2012; pp. 2578-2583; vol. 39, No. 5.

Weinberg; U.S. Appl. No. 61/804,094, filed Mar. 21, 2013.

* cited by examiner

METHOD AND APPARATUS FOR HIGH RESOLUTION PHYSIOLOGICAL IMAGING OF NEURONS

CROSS-REFERENCE TO RELATED APPLICATIONS

The present invention for precedence on the prior invention by I. N. Weinberg, U.S. Pat. No. 8,154,286, entitled "Apparatus and method for decreasing bio-effects of magnetic fields" (incorporated by reference in its entirety), and on continuations-in-patent applications filed by I. N. Weinberg, with Ser. Nos. 12/888,580, 12/905,256, and 13/439,382 (incorporated by reference in its entirety), and on U.S. Provisional Patent Application 61/804,094 filed by I. N. Weinberg (incorporated by reference in its entirety) and on U.S. Provisional Patent Application 61/652,223 filed by I. N. Weinberg (incorporated by reference in its entirety), and on U.S. Provisional Patent Application 61/074,397 filed by I. N. Weinberg (incorporated by reference in its entirety).

FIELD OF THE INVENTION

Disclosed embodiments are directed to describing the biochemistry, anatomy, and physiology of neurons with high spatial resolution, and to numerical simulations of such imaged distributions.

DESCRIPTION OF THE RELATED ART

Nanoparticles have been proposed as methods of assessing brain function (for example by Raymond Kurzweil, in The Futurist, March 2006, page 43). Several key challenges persist is attaining the effective spatial resolution to be able to characterize individual or small groups of neurons in a living being. It has been believed that magnetic resonance imaging of the human body in vivo will have a spatial resolution limit defined by the signal-to-noise ratio, on the order of 500 microns (as pointed out by E. DeVita, D. L. Thomas, S. Roberts, H. G. Parkes, R. Turner, P. Kinshesh, K. Shmueli, T. A. Yousry, and R. J. Ordridge, in the 2003 article published by the British Journal of Radiology, volume 76, pages 631-637, entitled "High resolution MRI of the brain at 4.7 Tesla using fast spin echo imaging") (incorporated by reference in its entirety). This spatial resolution is not adequate to separate individual neurons, which are between 4 and 100 microns in diameter.

SUMMARY

In accordance with disclosed embodiments, very high magnetic gradients and magnetic slew rates (for example, those enabled by the prior invention by I. N. Weinberg discussed herein) are applied to magnetizable particle imaging in order to realize high spatial resolution.

The particle design may incorporate sensing capabilities in order to report relevant physiological and anatomic attributes of neurons, including the case of in vivo measurements of the brain. Such reported measurements can be incorporated into computer simulations of neuronal function.

Additional features of the disclosure will become apparent to those skilled in the art upon consideration of the following detailed description of illustrated embodiments exemplifying the best mode of carrying out the disclosure as presently perceived.

BRIEF DESCRIPTION OF THE FIGURES

The detailed description particularly refers to the accompanying figures in which.

DETAILED DESCRIPTION

Figure 1:
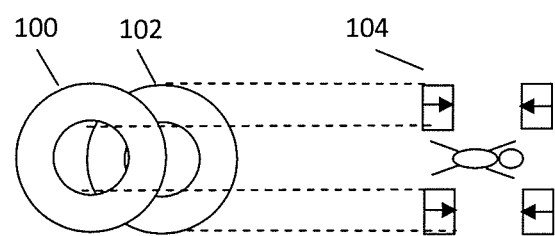
FIG. 1 is an illustration of an apparatus 101 used to impose magnetic gradients on living tissue.

In the current invention, the term "particle" or "nanoparticle" is intended to refer to artificial structures less than 100 microns in any one dimension, and preferably less than 1 micron is any one dimension. In the field of nanoparticles, the term "nano" typically implies that one of the dimensions is less than one micron. However, the division between "nano" and "micro" is not very relevant to the studies of living tissues, where cells and microbes range from tens of nanometers in size to tens of microns. The terms "magnetic particle" or "magnetizable particles" are used interchangeably in this disclosure, since in general the term "magnetic particle" actually refers to a particle which is not always magnetic, but which can be magnetized by an imposed magnetic field. The term magnetizable particle is intended to refer to a particle in which magnetizable material is present, even if the entire particle is not magnetizable.

Magnetic Particle Imaging (MPI) examines the distribution of magnetizable nanoparticles (between 5 and 300 nanometers in diameter) using magnetic gradients. In a 2012 online publication entitled "X-Space MPI: Magnetic Nanoparticles for Safe Medical Imaging" by P. W. Goodwill, E. U. Saritas, L. R. Croft, T. N. Kim, K. M. Krishnan, D. V. Schaffer, S. M. Conolly, in the journal Advanced Materials (DOI: 10.1002/ama.201200221) (incorporated by reference in its entirety), the spatial resolution of MPI is proportional to several factors, including the magnitude of the magnetic field gradient and the slew rate of the magnetic field gradient used to excite the nanoparticles. The slew rate is defined as the rate of change of the magnetic gradient in time. According to the article by Goodwill, the spatial resolution of MPI using currently-available nanoparticles and conventional magnetic slew rates is on the order of several millimeters.

It is known that particles can be used to report on physiologically-relevant attributes of living cells. An example of a particle whose fluorescent signal depends on local chemical concentration was given by J. N. Anker and R. Kopelman, in a 2003 article published by Applied Physics Letters (volume 82, number 7, pages 1102-1104), entitled "Magnetically modulated optical nanoprobes" (incorporated by reference in its entirety), and in the 2003 RC Press-published Biomedical Photonics Handbook, edited by Tuan Vo-Dinh, in the chapter by E. Monson, M. Brasuel, M. A. Philbert, and R. Kopelman, entitled "PEBBLE Nanosensors for Bioanalysis" (incorporated by reference in its entirety). It is known that nanosensors can report local chemical properties through changes in the nanosensor magnetic properties, as taught by M. Colombo, S. Ronchi, D. Monti, F. Corsi, E. Trabucchi, and D. Prosperi, in the 2009 article in the journal Analytical Biochemistry (volume 392, issue 1, pages 96-102), entitled "Femtomolar detection of autoantibodies by magnetic relaxation nanosensors" (incorporated by reference in its entirety).

It is known that the activity of neurons can be modeled with numerical simulations in a computer. Some have advocated that the entire brain can be simulated, as disclosed in the 2012 review comment by M. W. Waldrop in the journal Nature (volume 482, pages 456-458), entitled "Computer modeling: Brain in a box" (incorporated by reference in its entirety).

As disclosed by I. N. Weinberg in U.S. Pat. No. 8,154,286 (incorporated by reference in its entirety) and the related patent applications of I. N. Weinberg referred to above (and incorporated by reference in their entireties), and in the 2012 Medical Physics article (volume 39, issue 5) by I. N. Weinberg, P. Y. Stepanov, S. T. Fricke, R. Probst, M. Urdaneta, D. Warnow, H. D. Sanders, S. C. Glidden, A. McMillan, P. M. Starewicz, and J. P. Reilly, entitled "Increasing the oscillation frequency of strong magnetic fields above 101 kHz significantly raises peripheral nerve excitation thresholds" (incorporated by reference in its entirety), it was previously believed that it would not be possible to increase magnetic gradients in humans over a maximum threshold, or to increase magnetic slew rates in humans over a maximum threshold value, due to the resulting unpleasant nerve stimulation. However, the 2012 Medical Physics article by Weinberg et al cited above showed that the prior belief to be incorrect for magnetic pulses with sufficiently short rise- and fall-times (e.g., less than 10 microseconds), which exhibited no unpleasant nerve stimulation even at very high magnetic gradient field strengths (i.e., 0.4 Tesla).

For the purpose of this disclosure, either of the terms rise and fall times are lumped into the term "transition times", broadly describing the time period in which the magnitude and/or direction of the magnetic field gradient changes substantially (e.g., by more than 10 percent).

Disclosed embodiments apply the prior invention by Weinberg to the challenge of improving the spatial resolution of magnetic particle imaging, and (among other things) thereby leading to an improvement in computerized simulation of the neurons in the brain and nervous systems of humans and other animals.

As disclosed by I. N. Weinberg in U.S. patent application 61/804,094, entitled "Spatially-encoded nanostimulator" (incorporated by reference in its entirety), it is possible to power a particle externally, and stimulate a neuron or set of neurons in order to probe the function of the assembly of neurons. Alternatively, such a powered particle could be used to sense a local electric field, and report the status of the electric field to an antenna held external to the living tissue. The present invention contemplates use of such particles to report on the physiological status of neurons in a living being.

As illustrated in FIG. 1, an apparatus 101 includes at least one coil 100, 102 and at least one coil driver may be implemented using the methods and apparatuses previously described by Weinberg. These method and apparatuses may be configured in order to deliver a changing magnetic field gradient with very high slew rate and magnitude, as in FIG. 1, and without causing unpleasant stimulation to the subject.

FIG. 1 is an adaptation of the FIG. 1 by Goodwill et al, in which a body is inserted between gradient-producing coils 100, 102, seen from the side as 104. The rapidly changing strong magnetic field gradient is used (under the control of one or more controllers coupled to the coils 100, 102) to describe the location of a set of magnetic nanoparticles that have been previously introduced into neuronal tissue. Said description could be constituted into an image of the distribution of magnetic nanoparticles in the neuronal tissue. The introduction of the nanoparticles may be accomplished though intravenous injection, oral ingestion, intratympanic injection, or intranasal injection, or direct injection into neuronal tissue, or other means. The injection of nanoparticles may be accelerated through the introduction of an appropriately-directed magnetic field, as disclosed by I. N. Weinberg in U.S. provisional patent application 61/596,395, entitled "Magnetically-assisted delivery of therapeutic agents through barriers" (incorporated by reference in its entirety).

It should be understood that the maximum magnetic gradient slew rate may be, for example, greater than 1,000 Tesla/meter/second or greater than 10,000 Tesla/meter/second.

Additionally, the components of the system may assess the physiological status of the neurons by measuring the electromagnetic properties of at least one particle containing a magnetizable material with a sensor external to the tissue.

Spatial resolution may be sufficient to distinguish individual neurons. A distribution of neurons or a physiologic status and distribution of the neurons may be input into a computational simulation run on one or more computers.

Thus, the distribution of the neurons in the living tissue may be described without causing unpleasant stimulation.

The mechanism(s) for determining the location of one or more magnetizable particles in the neuronal tissue may be through magnetic particle imaging as described above by Goodwill and others. The magnetic nanoparticles may be sensitive to the chemical and/or physical properties of their local environment, whereby their response to the applied magnetic field may be used in order to describe the chemical or physical properties of the local environment.

One method of conferring such sensitivity to the local environment is to have conducting materials or dielectric materials incorporated into the particles, so that in the presence of a non-uniform electric field, the particles orient themselves through electrorotation and/or dielectrophoresis. A summary of dielectrophoresis and electrorotation is taught by T. B. Jones in the article entitled "Basic Theory of Dielectrophoresis and Electrorotation", published in the November/December 2003 edition of IEEE Engineering in Medicine and Biology Magazine, pages 33-42 (incorporated by reference in its entirety).

A neuron generates strong electric fields during polarization, which could result in selective directional orientation of the local particles. This orientation could be sensed through antennas held near the living being, as a result of the non-uniform magnetization of the particles.

Figure 2:
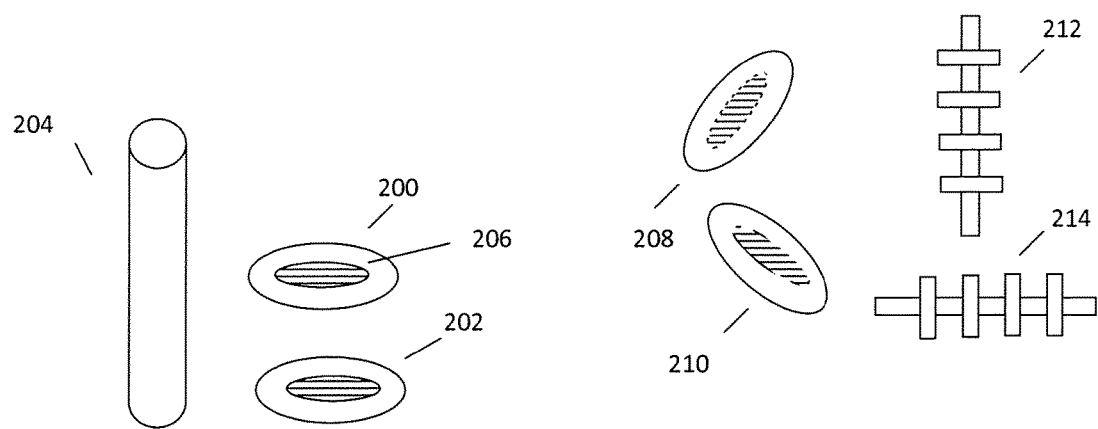
FIG. 2 is an illustration of a set of particles whose orientation depends on the local electric field.

FIG. 2 illustrates a set of such particles (200, 202) in the vicinity of a neuron (204) that has generated a local non-uniform electric field. Each of the particles contains some magnetizable material (206) as well as incorporating dielectric or electrically-conducting materials so that the particles may orient themselves through electrorotation and/or dielectrophoresis in the presence of a strong electric field. The orientation of particles (200, 202) in the vicinity of the electrically-active section of neuron (204) may be non-uniform, being aligned toward the electrically-active section of the neuron, as compared to particles farther from the neuron (208, 210) which are not uniformly-oriented.

It is understood that one preferential alignment of the particles with respect to the neuron might not be toward the neuron as shown in FIG. 2 but might be in some other direction. This non-uniform alignment of one or more particles may be detected by asymmetric signals from the particles sensed with directional antennas (212, 214) held external to the living tissue. For the purpose of this disclosure, the term "directional antenna" is used to describe a sensing device that is sensitive to particular orientations of electromagnetic waves. It is understood that many different types of antennas and sensors (for example, a superconducting quantum interference device) could take the place of the set of antennas (212, 214) shown in FIG. 2.

Figure 3:
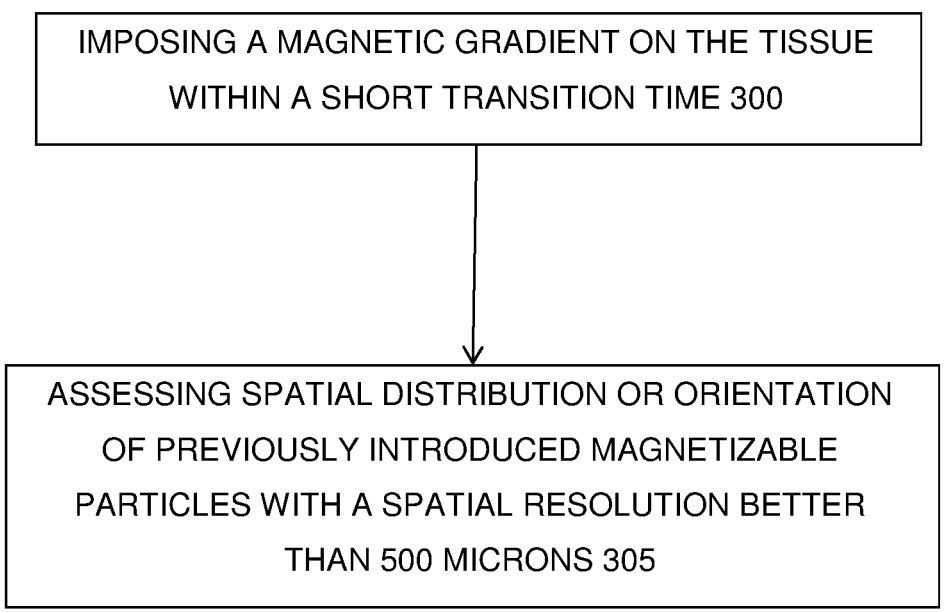
FIG. 3 is an illustrative flow chart of a method according to a disclosed embodiment.

The description of the status and anatomy of the set of magnetic nanoparticles may be input into a computational simulation as described above in order to develop a model of the neuronal function. In accordance with a disclosed method for describing the distribution of neurons in living tissue without causing unpleasant stimulation, and as shown in FIG. 3, the method comprises imposing a magnetic gradient on the tissue within a short transition time at 300. Subsequently, at 305, the spatial distribution or orientation of previously introduced magnetizable particles is assessed with a spatial resolution better than 500 microns. Note, the physiological status of the neurons may be assessed by measuring the electromagnetic properties of at least one particle containing a magnetizable material with a sensor external to the tissue. Further, the physiological status of the neurons may be assessed by measuring the orientation of at least one particle containing a magnetizable material with a sensor external to the tissue. Additionally, the physiological status and distribution of neurons may be input into a computational simulation.

Any of the above methods can be implemented using a tangible storage device such as a non-transitory computer readable storage device storing instructions which, when executed on one or more programmed processors, carry out a method. In this case, the term non-transitory is intended to preclude transmitted signals and propagating waves, but not storage devices that are erasable or dependent upon power sources to retain information.

Although not specifically illustrated, it should be understood that the components illustrated in FIG. 1 and their associated functionality may be implemented using one or more general purpose computers running software algorithms to provide the presently disclosed functionality and turning those computers into specific purpose computers.

Moreover, those skilled in the art will recognize, upon consideration of the above teachings, that the above exemplary embodiments may be based upon use of one or more programmed processors programmed with a suitable computer program. However, the disclosed embodiments could be implemented using hardware component equivalents such as special purpose hardware and/or dedicated processors. Similarly, general purpose computers, microprocessor based computers, micro-controllers, optical computers, analog computers, dedicated processors, application specific circuits and/or dedicated hard wired logic may be used to construct alternative equivalent embodiments.

Those skilled in the art will appreciate, upon consideration of the above teachings, that the program operations and processes and associated data used to implement certain of the embodiments described above can be implemented using disc storage as well as other forms of storage devices including, but not limited to non-transitory storage media (where non-transitory is intended only to preclude propagating signals and not signals which are transitory in that they are erased by removal of power or explicit acts of erasure) such as for example Read Only Memory (ROM) devices, Random Access Memory (RAM) devices, network memory devices, optical storage elements, magnetic storage elements, magneto-optical storage elements, flash memory, core memory and/or other equivalent volatile and nonvolatile storage technologies without departing from certain embodiments of the present invention. Such alternative storage devices should be considered equivalents.

Certain embodiments described herein, are or may be implemented using a programmed processor executing programming instructions that are broadly described above in flow chart form that can be stored on any suitable electronic or computer readable storage medium. However, those skilled in the art will appreciate, upon consideration of the present teaching, that the processes described above can be implemented in any number of variations and in many suitable programming languages without departing from embodiments of the present invention. For example, the order of certain operations carried out can often be varied, additional operations can be added or operations can be deleted without departing from certain embodiments of the invention. Error trapping, time outs, etc. can be added and/or enhanced and variations can be made in user interface and information presentation without departing from certain embodiments of the present invention. Such variations are contemplated and considered equivalent.

While certain illustrative embodiments have been described, it is evident that many alternatives, modifications, permutations and variations will become apparent to those skilled in the art in light of the foregoing description. While illustrated embodiments have been outlined above, it is evident that many alternatives, modifications and variations will be apparent to those skilled in the art. Accordingly, the various embodiments of the invention, as set forth above, are intended to be illustrative, not limiting. Various changes may be made without departing from the spirit and scope of the invention.

As a result, it will be apparent for those skilled in the art that the illustrative embodiments described are only examples and that various modifications can be made within the scope of the invention as defined in the appended claims.

The invention claimed is:

1. A method for providing an effective spatial resolution for imaging magnetizable particles for characterizing of neurons in living tissue without causing peripheral nerve stimulation, the method comprising:
   introducing magnetizable particles into living tissue;
   applying a magnetic gradient on the living tissue within a transition time of less than one millisecond; and
   assessing a physiological status of the neurons by measuring the spatial distribution or orientation of the previously introduced magnetizable particles with a spatial resolution smaller than 500 microns,
   wherein the assessment of the physiological status of the neurons is performed by measuring electromagnetic properties and/or orientation of at least one of the magnetizable particles using a sensor external to the living tissue, the sensor including at least one coil and at least one driver for imaging magnetizable particles.

2. The method of claim 1, where the transition time is less than 250 microseconds.

3. The method of claim 1, where the transition time is less than 100 microseconds.

4. The method of claim 1, where the transition time is less than 50 microseconds.

5. The method of claim 1, where the transition time is less than 10 microseconds.

6. The method of claim 1, where a maximum magnitude of the magnetic gradient is greater than 100 milliTesla.

7. The method of claim 1, where a maximum magnitude of the magnetic gradient is greater than 400 milliTesla.

8. The method of claim 1, where a maximum magnetic gradient slew rate is greater than 1,000 Tesla/meter/second.

9. The method of claim 1, where a maximum magnetic gradient slew rate is greater than 10,000 Tesla/meter/second.

10. The method of claim 1, wherein the distribution of the neurons is input into a computational simulation.

11. The method of claim 1, where the physiological status and distribution of the neurons is input into a computational simulation.

12. The method of claim 1, where the orientation of at least one particle is influenced by electromagnetic fields in the vicinity of one or more neurons, wherein the orientation is sensed external to the living tissue.

13. The method of claim 1, where the spatial resolution is sufficient to distinguish individual neurons.

14. An apparatus configured to provide an effective spatial resolution for imaging magnetizable particles for characterizing neurons in living tissue without causing peripheral nerve stimulation, the apparatus comprising:

application coils and drivers configured to apply a magnetic field to the living tissue with a transition time of less than one millisecond; and imaging coils and drivers configured to assess a physiological status of the neurons by measuring the spatial distribution or orientation of previously introduced magnetizable particles with a spatial resolution smaller than 500 microns, wherein the assessment of the physiological status of the neurons is performed by measuring electromagnetic properties and/or orientation of at least one of the magnetizable particles using the imaging coils and drivers that are external to the living tissue to perform imaging of magnetizable particles.

15. An apparatus configured to probe a function of one or more neurons in living tissue without causing peripheral nerve stimulation, the apparatus comprising:

application coils and drivers for applying a magnetic gradient to the living tissue with a transition time smaller than 500 microns, and at least one sensor including detecting coils and drivers for detecting signals emitted by at least one previously introduced particle containing magnetizable material, the emitted signals depending on the function of one or more neurons.

* * * * *